(12) United States Patent
Lee et al.

(10) Patent No.: US 7,582,306 B2
(45) Date of Patent: Sep. 1, 2009

(54) PSEUDOCERAMIDES AND COSMETIC COMPOSITIONS COMPRISING THE SAME

(75) Inventors: Jung-No Lee, Chungcheongnam-do (KR); Kang-Tae Lee, Cheonan-shi (KR); Jee-Hean Jeong, Suwon-shi (KR); Byong-Kee Jo, Anyang-shi (KR)

(73) Assignee: Coreana Cosmetics Co., Ltd., Cheonan-shi (KR)

( * ) Notice: Subject to any disclaimer, the term of this patent is extended or adjusted under 35 U.S.C. 154(b) by 908 days.

(21) Appl. No.: 10/505,758

(22) PCT Filed: Feb. 26, 2002

(86) PCT No.: PCT/KR02/00314

§ 371 (c)(1),
(2), (4) Date: Nov. 4, 2004

(87) PCT Pub. No.: WO03/072540

PCT Pub. Date: Sep. 4, 2003

(65) Prior Publication Data

US 2005/0118131 A1    Jun. 2, 2005

(51) Int. Cl.
*A61K 8/02* (2006.01)
*A61K 311/33* (2006.01)
*C07C 231/08* (2006.01)
*C07C 233/31* (2006.01)

(52) U.S. Cl. ............... 424/401; 554/35; 554/40; 554/42; 554/44; 554/61; 554/66; 514/613; 514/663; 514/665; 514/667

(58) Field of Classification Search ............ None
See application file for complete search history.

(56) References Cited

U.S. PATENT DOCUMENTS

| 5,175,321 A | 12/1992 | Ohashi et al. |
| 5,206,020 A | 4/1993 | Critchley et al. |

FOREIGN PATENT DOCUMENTS

| DE | 195 39 016 A1 | 4/1996 |
| EP | 0 209 158 A2 | 1/1987 |
| EP | 0 482 860 A1 | 4/1992 |
| EP | 0 495 624 A1 | 7/1992 |
| WO | WO 00/62745 * | 10/2000 |
| WO | 03/037845 A1 | 5/2003 |

OTHER PUBLICATIONS

Fulmer et al; "Stratum Corneum Lipid Abnormalities in Surfactant-Induced Dry Scaly Skin"; The Society for Investigative Dermatology, Inc., 1986, pp. 598-602.

* cited by examiner

Primary Examiner—Patricia A Duffy
Assistant Examiner—Anna Pagonakis
(74) Attorney, Agent, or Firm—Nixon & Vanderhye P.C.

(57) ABSTRACT

The present invention relates to a pseudoceramide represented by the following formula (I) and a cosmetic composition comprising the same:

$$\text{(I)}$$

[Structural formula showing a branched hydrocarbon chain with four $CH_3$ branches, terminating in groups labeled Z, Y, X]

wherein Z represents —OH and Y represents —OH, $$-O-\overset{\overset{O}{\|}}{\underset{\underset{OH}{|}}{P}}-OH \quad \text{or} \quad -O-\overset{\overset{O}{\|}}{\underset{\underset{O}{\|}}{S}}-OH$$

with the proviso that X is $$\overset{O}{\underset{HN}{\|}}\!\!\diagup\!\!\diagdown_{R};$$

Z represents —OH and X represents —OH, $$-O-\overset{\overset{O}{\|}}{\underset{\underset{OH}{|}}{P}}-OH \quad \text{or} \quad -O-\overset{\overset{O}{\|}}{\underset{\underset{O}{\|}}{S}}-OH$$

with the proviso that Y is $$\overset{O}{\underset{HN}{\|}}\!\!\diagup\!\!\diagdown_{R};$$

Y represents —OH and X represents —OH, $$-O-\overset{\overset{O}{\|}}{\underset{\underset{OH}{|}}{P}}-OH \quad \text{or} \quad -O-\overset{\overset{O}{\|}}{\underset{\underset{O}{\|}}{S}}-OH$$

with the proviso that Z is $$\overset{O}{\underset{HN}{\|}}\!\!\diagup\!\!\diagdown_{R};$$

R represents a linear or branched, saturated or unsaturated aliphatic hydrocarbon group; and when substituted, R has one or more —OH groups.

5 Claims, No Drawings

PSEUDOCERAMIDES AND COSMETIC COMPOSITIONS COMPRISING THE SAME

This application is the US national phase of international application PCT/KR02/00314 filed 26 Feb. 2002, which designated the US, the entire contents of this application is incorporated herein by reference.

BACKGROUND OF THE INVENTION

1. Field of the Invention

The present invention relates to novel pseudoceramides and cosmetic compositions comprising the same. More particularly, the present invention relates to novel pseudoceramides showing excellent permeability barrier similar to that found in natural ceramides and improved water solubility and cosmetic compositions comprising the same as active ingredient.

2. Description of the Related Art

The stratum corneum, which is located on the outermost side of the skin, serves a primary protection barrier from external irritation and invasion of foreign substances and maintains the moisture in the skin through intercellular lipids.

The intercellular lipids comprise ceramides, cholesterol, free fatty acids and neutral lipids, etc. and it has been found that ceramides is contained in the amount ranging from 40 to 50% and the most pivotal lipids in the intercellular lipids. It has been reported that the decrease of ceramide production caused by some genetic factors or aging is responsible for the weakening of barrier function of stratum corneum, thereby leading to adverse effects on the skin, e.g. atopic dermatitis and psoriasis (Fulmer & Kramer, *J. Invest. Derm.*, 86:598-602(1986); and Tupker R. A. et al., *Acta Derm. Venereol. Stockh*, 70:1-5(1990)).

Under such circumstances, many researches have focused on development of process for preparing natural or synthetic ceramides with greater efficiency and of novel pseudoceramides. The conventional process for preparing ceramides includes extraction method (from animal, plant or yeast) and chemical synthetic method.

Naturally occurring ceramides show superior function but inferior application to cosmetic compositions due to lower solubility, finally resulting in high production cost.

Therefore, there remains a need in the art for novel synthetic ceramides with excellent water barrier function, exhibiting improved applicability to cosmetic composition, which can be synthesized at relatively low cost.

U.S. Pat. No. 5,206,020 discloses novel synthetic pseudoceramide prepared by ring opening the epoxide ring of a glycidyl ether with $RNH_2$ to yield the corresponding secondary amine and then acylating the secondary amine. In addition, U.S. Pat. No. 5,175,321 discloses novel pseudoceramide synthesized in such a manner that certain compound prepared from glycidyl ether and ethanolamine is reacted with a fatty acid lower alkyl ester.

Throughout this application, various patents are reference and citations are provided in parentheses. The disclosure of these patents in their entities are hereby incorporated by references into this application in order to more fully describe this invention and the state of the art to which this invention pertains.

SUMMARY OF THE INVENTION

To be free from the shortcomings of natural and conventional synthetic ceramides aforementioned, the inventors have researched to develop novel pseudoceramide. As a result, the inventors have developed novel pseudoceramide prepared in feasible manner and with lower production cost.

Accordingly, it is an object of this invention to provide novel pseudoceramides.

It is another object of this invention to provide cosmetic compositions comprising the novel pseudoceramides as active ingredient.

Other objects and advantages of the present invention will become apparent from the detailed description to follow taken in conjugation with the appended claims.

DETAILED DESCRIPTION OF THIS INVENTION

In one aspect of this invention, there is provided a novel pseudoceramide represented by the following formula (I):

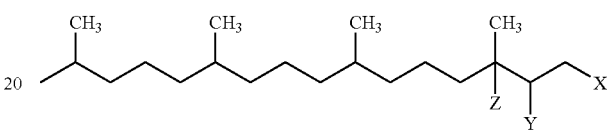
(I)

wherein Z represents —OH and Y represents —OH,

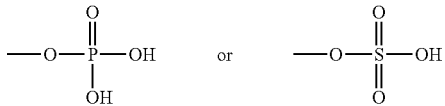

with the proviso that X is

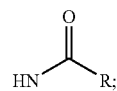

Z represents —OH and X represents —OH,

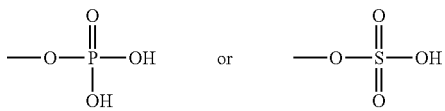

with the proviso that Y is

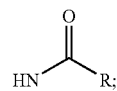

Y represents —OH and X represents —OH,

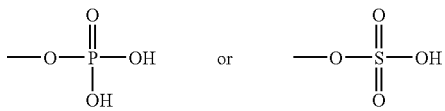

with the proviso that Z is

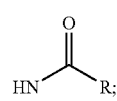

R represents a linear or branched, saturated or unsaturated aliphatic hydrocarbon group; and when substituted, R has one or more —OH groups.

The pseudoceramides of this invention can be prepared using unique starting materials with lower production cost, which is exemplified in Examples below. The starting materials employed for synthesizing the pseudoceramides of this invention have been provided by the inventors, which is disclosed in PCT/KR01/01838.

According to preferred embodiment of this invention, R group found in formula (I) is a linear or branched, saturated or unsaturated aliphatic hydrocarbon group and when substituted, it has one or more —OH groups.

The term "aliphatic hydrocarbon group" used herein refers to all hydrocarbon groups (for example, alkyl, alkenyl or alkynyl groups) except aromatic hydrocarbon.

As provided herein, the term "alkyl" is defined to be linear or branched chain saturated aliphatic hydrocarbon group having designated carbon atoms, including methyl, ethyl, n-propyl, isopropyl, n-butyl, n-hexyl, nonyl, decyl, hexadecyl, eicosyl, triacontyl and tetracontyl, but not limited to.

The term used herein "alkenyl" refers to linear or branched chain unsaturated aliphatic hydrocarbon group having designated carbon atoms, including ethenyl, propenyl, n-pentenyl, nonenyl, decenyl, hexadecenyl, eicosenyl, triacontenyl and tetraontenyl, but not limited to.

Exemplified pseudoceramide of this invention is represented by the following formula (II), (III) or (IV):

In another aspect of this invention, there is provided a method for preparing the pseudoceramide represented by the above formula (I), which comprises the steps of: (a) preparing phytandiol amine derivative of the formula (V); and

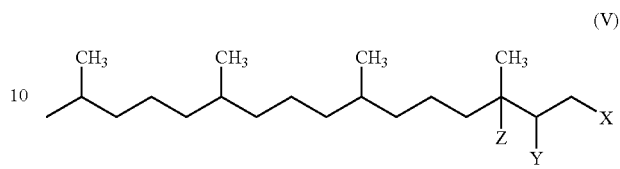

wherein each of Y and Z is OH with the proviso that X is $NH_2$, each of X and Z is OH with the proviso that Y is $NH_2$, and each of X and Y is OH with the proviso that Z is $NH_2$, (b) preparing the pseudoceramide represented by the above formula (I) by reacting the phytandiol amine derivative of the formula (V) with aliphatic hydrocarbon compound.

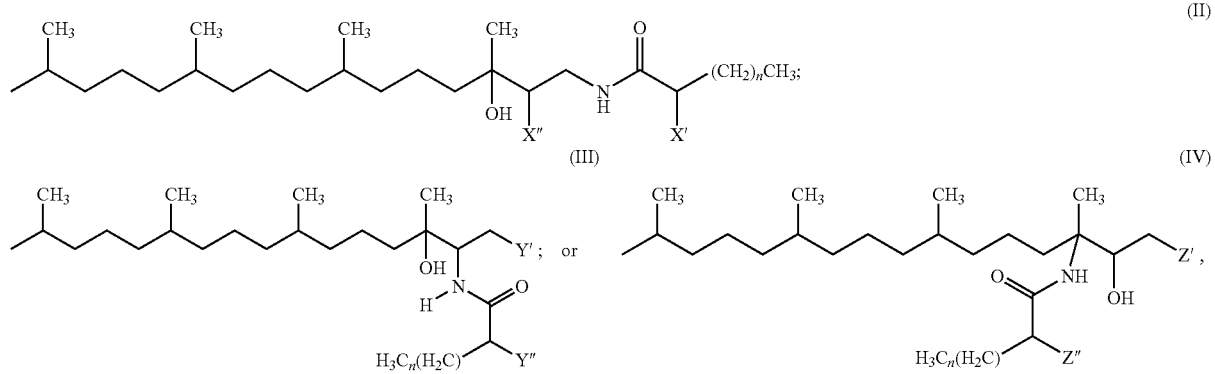

wherein X' represents H or —OH; X" represents —OH,

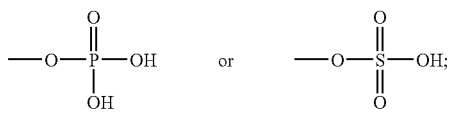

Y' represents —OH,

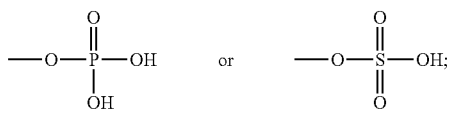

Y" represents H or —OH; Z' represents —OH,

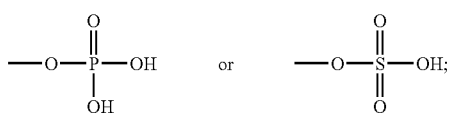

Z" represents H or —OH; and n is 0 or an integer of from 1 to 47.

In the process of this invention, the step of preparing phytandiol amine derivative is exemplified in Examples and PCT/KR01/01838.

The second step of the present method is one to form amide bond, which is exemplified in Examples, and can be carried out according to a variety of methods. For example, in the case of using carboxylic acid compound, the carboxylic group of the compound is primarily activated with p-toluenesulfonylchloride or benzenesulfonylchloride (generally, in the presence of basic catalyst, e.g., triethylamine) and the resultant is reacted with the phytandiol amine derivative of the formula (V) to generate amide bond, thereby obtaining the pseudoceramide of the present invention.

Alternatively, the lactone compound can be employed in place of the carboxylic acid compound.

In still another aspect of this invention, there is provided a cosmetic composition for skin care comprising (a) the pseudoceramide of this invention as active ingredient; and (b) a cosmetically acceptable carrier.

In the present composition, it is general that the pseudoceramide is present in an amount of 0.0001-10.0 wt % based on the total weight of the composition. The preferred amount of the pseudoceramide is 0.0005-10.0 wt % and more preferably, 0.005-10 wt %. If the amount is less than 0.0001 wt %, a moisturizing maintenance effect may be negligible; and in the case of exceeding 10 wt %, the increase of moisturizing maintenance effect in parallel with the increase of amount may be rarely represented.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray.

The cosmetically acceptable carrier contained in the present cosmetic composition, may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonites, silica, talc, zinc oxide or mixtures of these substances. In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, in particular cottonseed oil, groundnut oil, maize germ oil, olive oil, castor oil and sesame seed oil, glycerol fatty esters, polyethylene glycol and fatty acid esters of sorbitan or mixtures of these substances. The formulation of suspension may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these substances.

The formulation of soap may comprise alkali metal salts of fatty acids, salts of fatty acid hemiesters, fatty acid protein hydrolyzates, isethionates, lanolin, fatty alcohol, vegetable oil, glycerol, sugars or mixtures of these substances.

Furthermore, the cosmetic compositions of this invention, may contain auxiliaries as well as carrier. The non-limiting examples of auxiliaries include preservatives, antioxidants, stabilizers, solubilizers, vitamins, colorants, odor improvers or mixtures of these substances The compositions of this invention are significantly effective in enhancing moisturizing maintenance capacity of skin resulting from the pseudoceramide prepared in this invention, thereby treating, alleviating and preventing atopic dermatitis and psoriasis.

The following specific examples are intended to be illustrative of the invention and should not be construed as limiting the scope of the invention as defined by appended claims.

EXAMPLE

Example I

Preparation of Phytandiol Amine Derivative [I]

In a reactor 0.3 g of phytantriol (0.91 mmol, Sigma-Aldrich) was dissolved in 20 ml of normal hexane and stirred for 10 min. at a room temperature, followed by addition of 0.21 g (1.09 mmol) of para-toluene sulfonylchloride (Sigma-Aldrich). Following the drop of the temperature of the reactor to 0° C., 0.11 g (1.09 mmol) of triethyl amine and a catalytic amount of pyridine were added dropwise and the temperature of the reactor was elevated to a room temperature, followed by stirring for 12 hr. Upon the completion of the reaction, the solvent was removed by distillation under reduced pressure. Then, 20 ml of chloroform was added to the concentrate for extraction and the extract was washed with saline. The washed extract was dried over anhydrous magnesium sulfate, followed by filtration and concentration to yield 0.48 g para-toluene sulfonyl phytandiol derivative as brown oil.

The yielded phytandiol derivative (0.48 g) was dissolved in 25 ml of dimethyl formamide and 0.06 g (1.00 mmol) of sodium azide (Sigma-Aldrich) was added, followed by reflux for 5 hr in order to substitute azide for para-toluene sulfonyl group. The reaction mixture was extracted with 50 ml of methylene chloride solution and washed with saline. Following drying over anhydrous magnesium sulfate, filtration and concentration, 0.29 g of azido phytandiol derivative was yielded.

In order to convert the azido phytandiol derivative to amine compound, 0.29 g of the yielded azido phytandiol (8.4 mmol) was subject to hydrogenation in ethyl alcohol with a catalytic amount of 10% palladium charcoal under 50 psi of hydrogen atmosphere for 3-4 hr, and finally 0.21 g of phytandiol amine derivative [I] (0.64 mmol) was obtained in the form of yellow gel in the overall yield of 70%: Anal. Calcd. for $C_{20}H_{43}NO_2$ (329.33): C, 72.89; H, 13.15; N, 4.25; O, 9.71; Found C, 72.63; H, 13.42; N, 4.13; O, 9.55.

The reactions in this Example is schematically illustrated as follows:

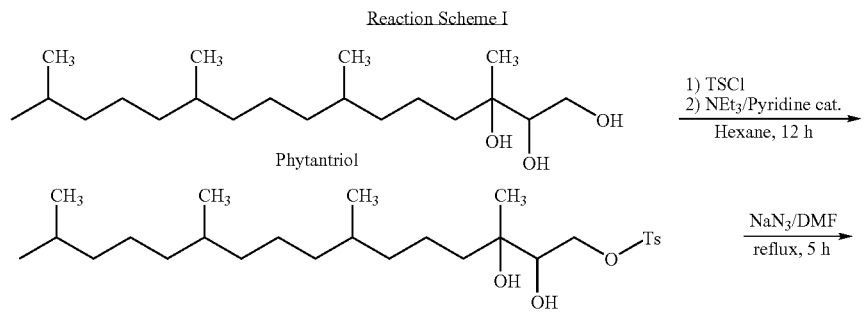

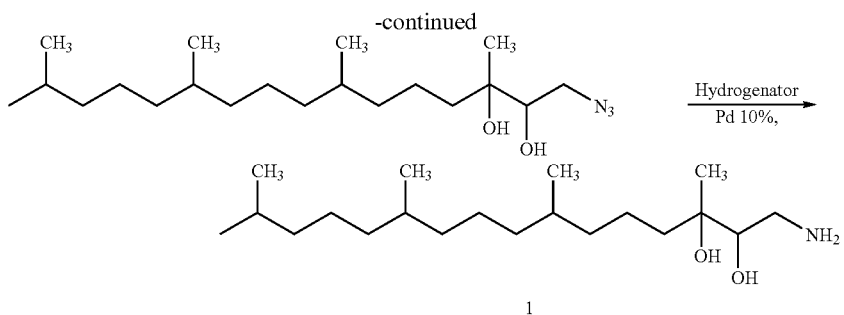

Example II

Preparation of Phytandiol Amine Derivative [II]

In a reactor 0.3 g of phytol (1.0 mmol, Sigma-Aldrich) was dissolved in 30 ml of methylene chloride and then the temperature of the reactor was decreased to 0° C. While maintaining the temperature of the reactor, to the mixture was added 0.45 g of 77% chloroperoxy benzoic acid (Sigma-Aldrich). After the completion of the reaction, the resultant was extracted with 50 ml of chloroform to prepare phytol derivative epoxidated at 2- and 3-positions. The phytol derivative was reacted with ammonia gas for 5 hr. to produce 0.21 g of phytandiol amine derivative [II] in the yield of 64%: Anal. Calcd. for $C_{20}H_{43}NO_2$ (329.33): C, 72.89; H, 13.15; N, 4.25; O, 9.71; Found C, 72.44; H, 13.51; N, 4.65; O, 9.98.

The reactions in this Example is schematically illustrated as follows:

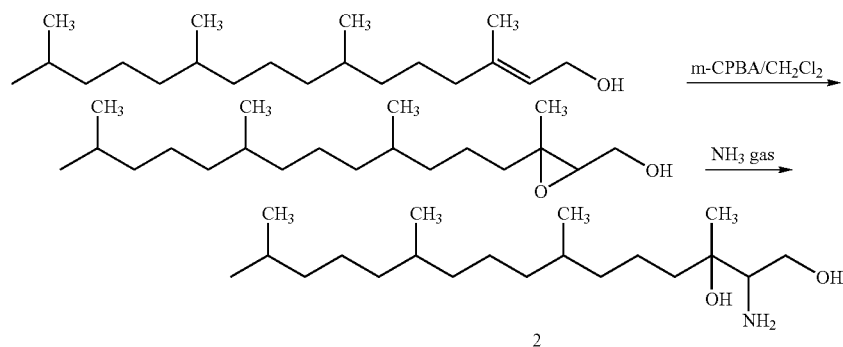

Example III

Preparation of Phytandiol Amine Derivative [III]

One g of phytantriol (3.0 mmol, Sigma-Aldrich) was refluxed using deanstock apparatus for 15 hr in 25 ml of acetone solution with toluene sulfonic acid as catalyst. After the completion of the reaction, the acetone solvent was removed under reduced pressure and the resultant was extracted with chloroform solution. The extract was washed with saturated sodium bicarbonate solution and was again washed with saline to obtain 0.3 g of (2-(2,2-dimethyl-[1,3] dioxolan-4-yl)-6,10,14-trimethyl-pentadecan-2-ol) of which 1- and 2-positions were protected.

Thereafter, in 20 ml of normal hexane was dissolved 0.3 g of (2-(2,2-dimethyl-[1,3]dioxolan-4-yl)-6,10,14-trimethyl-pentadecan-2-ol), and stirred for 10 min. at a room temperature, followed by addition of 0.18 g (0.97 mmol) of para-toluene sulfonylchloride. After the drop of the temperature of the reactor to 0° C., 3 equivalents of pyridine were added and the temperature of the reactor was elevated to a room temperature, followed by stirring for 12 hr. Upon the completion of the reaction, the solvent was removed by distillation under reduced pressure. Then, 20 ml of chloroform was added to the concentrate for extraction and the extract was washed with saline. The washed extract was dried over anhydrous magnesium sulfate, followed by filtration and concentration to yield 0.41 g of a compound substituted at 3-position with toluene sulfonyl in the form of yellow oil. In 20 ml of 2N HCl was dissolved 0.41 g of the yellow oil, and then was reacted for 6 hr at 80° C. to yield 0.21 g of 1,2-phytandiol derivative of which ring structure is cleaved.

The phytandiol derivative yielded (0.21 g) was dissolved in 25 ml of dimethyl formamide and 0.06 g (1.00 mmol) of sodium azide was added, followed by reflux for 5 hr to produce 0.15 g of phytandiol derivative substituted with azide. In order to reduce the azide-substituted phytandiol derivative to amine compound, 0.15 g of the azido phytandiol yielded was subject to hydrogenation in ethyl alcohol with a catalytic amount of 10%; palladium charcoal under 50 psi of hydrogen atmosphere for 3-4 hr, and finally 0.20 g of phytandiol amine derivative [III] was obtained in the yield of 60%: Anal. Calcd. for $C_{20}H_{43}NO_2$ (329.33): C, 72.89; H, 13.15; N, 4.25; O, 9.71; Found C, 72.51; H, 13.04; N, 4.54; O, 9.43.

The reactions in this Example is schematically illustrated as follows:

Reaction Scheme III

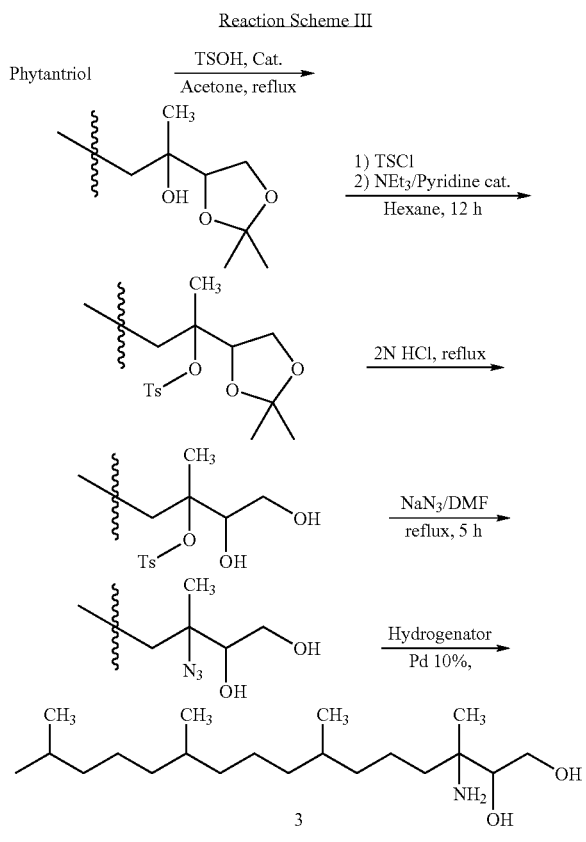

Example IV

Preparation of Novel Pseudoceramide 4

To synthesize pseudoceramide derivative of this invention using phytandiol amine derivative I prepared in Example I, 100 ml of anhydrous chloroform and stearic acid (36.3 mmol) were mixed in a reactor and agitated at room temperature until stearic acid was completely dissolved. After the completion of dissolution, p-toluenesulfonylchloride (36.3 mmol) was added and agitated for 5 min., followed by adding dropwise triethylamine as base (36.3 mmol). Upon the addition of triethylamine, the resultant was agitated for 30 min at room temperature.

Then, phytandiol amine derivative I (30.2 mmol) was dissolved in 10 ml of chloroform and the solution yielded was added to the resultant, followed by allowing for reaction at room temperature. The reaction was tracked with TLC (thin layer chromatography) in order to determine the completion of reaction. Following the completion of the reaction, the reaction mixture was washed with distilled water (150 ml×3) and then saline (150 ml). Washed organic layer was subject to the distillation under reduced pressure, and to the concentrated residue obtained thus, 50 ml of absolute acetone were added, followed by recrystallization at 0° C. The resultant was filtered through Whatman Paper No. 5 and dried to yield 12.5 g of pseudoceramide 4 (octadecanoic acid (2,3-dihydroxy-3,7,11,15-tetramethyl-hexadecyl)amide) in the form of white solid in the overall yield of 69.5%: m.p. 47-48° C.; IR (cm$^{-1}$) 3430, 2950, 2600, 2500, 1700, 1480; Anal. Caclc. For $C_{38}H_{77}NO_3$ (595.59): C, 76.58; H, 13.02; N, 2.35; O, 8.05; found C, 76.51; H, 13.04; N, 2.54; O, 8.43.

The reactions in this Example are schematically illustrated as follows:

Reaction Scheme IV

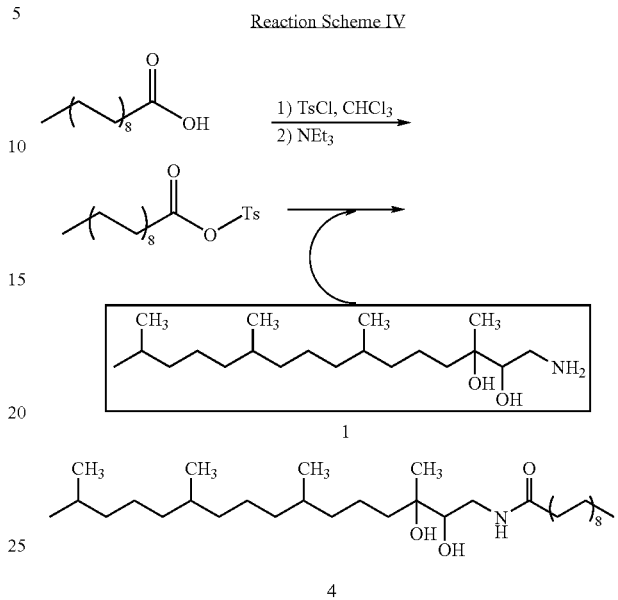

Example V

Preparation of Novel Pseudoceramide 5

According to the method described in M. Merritt. et al. *JACS.*, 120:8494-8501(1998), the hydroxyl group at the position of 2 was substituted with sulfate group. To a reactor containing 0.34 mmol of pseudoceramide 4 in 20 ml of chloroform, 1.02 mmol of sulfur trioxide pyridine complex were added and agitated for 14 hr at room temperature. The reaction progress was tracked with TLC and then 20 ml of chloroform were added to terminate the reaction following the completion of reaction. Thereafter, the resultant was cooled to −10° C. and filtered. The yielded residue was concentrated and then recrystallized in acetone solution, thereby obtaining 0.18 g of pseudoceramide 5 (octadecanoic acid(2-sulfate,3-hydroxy-3,7,11,15-tetramethylhexadecyl)amide) in the overall yield of 79%: Anal. Caclc. For $C_{38}H_{77}NO_6S$ (675.55): C, 67.51; H, 11.48; N, 2.07; O, 14.20; S, 4.74; found C, 67.03; H, 11.87; N, 2.43; O, 14.34; S, 4.67.

The reactions in this Example are schematically illustrated as follows:

Reaction Scheme V

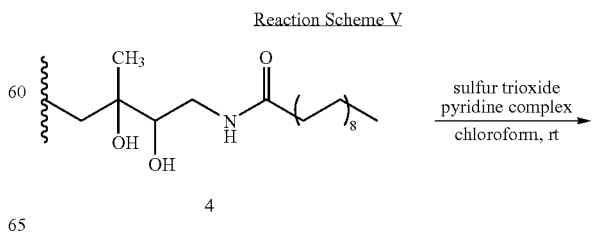

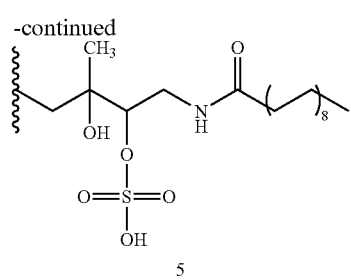

Example VI

Preparation of Novel Pseudoceramide 6

To 100 ml of anhydrous chloroform contained a reaction, oleic acid (36.3 mmol) was added and agitated at room temperature until the oleic acid was completely dissolved. After the completion of dissolution, p-toluenesulfonylchloride (36.3 mmol) was added and agitated for 5 min., followed by adding dropwise triethylamine as base (36.3 mmol). Upon the addition of triethylamine, the resultant was agitated for 30 min at room temperature.

Then, phytandiol amine derivative I (30.2 mmol) was dissolved in 10 ml of chloroform and the solution yielded was added to the resultant, followed by allowing for reaction at room temperature. The reaction was tracked with TLC and then the completion of reaction was determined. Following the completion of the reaction, the reaction mixture was washed with distilled water (150 ml). Washed organic layer was subject to the distillation under reduced pressure, and to the concentrated residue obtained thus, 50 ml of absolute acetone were added, followed by recrystallization at 0° C. The resultant was filtered through Whatman Paper No. 5 and dried to yield 1.10 g of pseudoceramide 6 (Octadec-9-enoic acid [1-(1'2'-dihydroxy-ethyl)-1,5,9,13-tetramethyl-tetradecyl]-amide) in the form of white solid in the overall yield of 61.5%: Anal. Caclc. For $C_{37}H_{73}NO_3$ (579.56):C, 76.62; H, 12.69; N, 2.42; O, 8.28; found C, 76.51; H, 13.01; N, 2.63; O, 8.51.

The reactions in this Example are schematically illustrated as follows:

Reaction Scheme VI

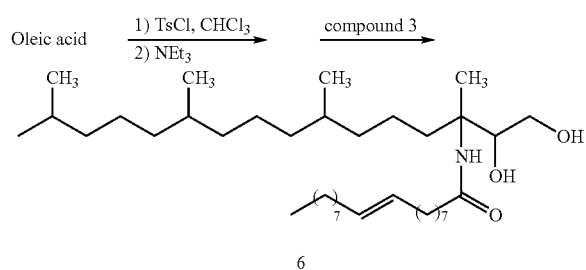

Example VII

Preparation of Novel Pseudoceramide 7

The pseudoceramide 6 (1.0 mmol) obtained in Example VI was dissolved in 20 ml of methylene chloride solution. To the resulting solution, a catalytic amount of DCC (1,3-dicyclohexylcarbodiimide, 1.2 mmol) and DMAP (4-Dimethylaminopyridine) were added and then agitated for 10 min. Phosphoric acid (2.5 mmol) was added to the reaction mixture and then agitated for 4 hr, after which the reaction was terminated with $KHCO_3$.

Following the completion of the reaction, the resultant was washed with distilled water (150 ml×3) and then saline (150 ml). Washed organic layer was subject to the distillation under reduced pressure, and to the concentrated residue obtained thus, 50 ml of absolute acetone were added, followed by recrystallization at 0° C. The resultant was filtered through Whatman Paper No. 5 and dried to yield 0.40 g of pseudoceramide 6 (Octadec-9-enoic acid [1-(1-hydroxy-2-phosphate-ethyl-1,5,9,13-tetradecyl)-amide) in the form of white solid in the overall yield of 60.9%: Anal. Caclc. For $C_{36}H_{71}NO_3P$ (579.56) :C, 67.04; H, 11.10; N, 2.17; O, 14.88; P, 4.80; found C, 67.51; H, 11.01; N, 2.53; O, 14.51; P, 4.56.

The reactions in this Example are schematically illustrated as follows:

Reaction Scheme VII

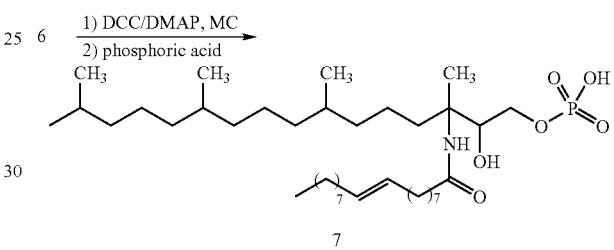

FORMULATION EXAMPLE

The following exemplified compositions were formulated according to conventional methods, which comprise the pseudoceramide 4 of this invention as active ingredient while the formulated compositions can be also applied to other pseudoceramide derivatives of this invention. Therefore, those skilled in the art will promptly recognize appropriate variations from the formulations both as to ingredients and as to the amount thereof.

Formulation I

Formulation I comprising the pseudoceramide 4 was prepared in the form of soft cosmetic liquid (skin lotion), of which composition is found in Table 1.

TABLE 1

| Ingredients | Amount (wt %) |
| --- | --- |
| Pseudoceramide 4 | 0.5 |
| 1,3-butylene glycol | 5.2 |
| Oleyl alcohol | 1.5 |
| Ethanol | 3.2 |
| Polysorbate 20 | 3.2 |
| Benzophenone-9 | 2.0 |
| Carboxylvinyl polymer | 1.0 |
| Glycerine | 3.5 |
| Tween 60 | 1.2 |
| Perfume | Minute quantity |
| Preservative | Minute quantity |
| Distilled water | To 100 |

Formulation II

Formulation II comprising the pseudoceramide 4 was prepared in the form of milk lotion, of which composition is found in Table 2.

TABLE 2

| Ingredients | Amount (wt %) |
| --- | --- |
| Pseudoceramide 4 | 0.6 |
| Glycerine | 5.1 |
| Propylene glycol | 4.2 |
| Tocopheryl acetate | 3.0 |
| Liquid paraffin | 4.6 |
| Stearic acid | 1.0 |
| Squalene | 3.1 |
| 1,3-butylene glycol | 2.5 |
| Polysorbate 60 | 1.6 |
| Sepigel 305 | 1.6 |
| Lipoid | 0.6 |
| Waglinol 31918 | 1.5 |
| Perfume | Minute quantity |
| Preservative | Minute quantity |
| Distilled water | To 100 |

Formulation III

Formulation III comprising the pseudoceramide 4 was prepared in the form of nutrient cosmetic cream, of which composition is found in Table 3.

TABLE 3

| Ingredients | Amount (wt %) |
| --- | --- |
| Pseudoceramide 4 | 1.0 |
| Glycerine | 4.0 |
| Vaseline | 3.5 |
| Triethanol amine | 2.1 |
| Liquid paraffin | 5.3 |
| Squalene | 3.0 |
| Wax | 2.6 |
| Tocophery acetate | 5.4 |
| Polysorbate 60 | 3.2 |
| Carboxyvinyl polymer | 1.0 |
| Sorbitan sesquinoleate | 3.1 |
| Perfume | Minute quantity |
| Preservative | Minute quantity |
| Distilled water | To 100 |

Formulation IV

Formulation IV comprising the pseudoceramide 4 was prepared in the form of pack, of which composition is found in Table 4.

TABLE 4

| Ingredients | Amount (wt %) |
| --- | --- |
| Pseudoceramide 4 | 1.0 |
| Ethyl alcohol | 3.0 |
| EDTA-2Na | 0.02 |
| Propylene glycol | 5.1 |
| Glycerine | 4.5 |
| Carbopol | 1.0 |
| Polyoxide | 0.1 |
| Perfume | Minute quantity |
| Preservative | Minute quantity |
| Distilled water | To 100 |

Comparative Formulation I

Comparative formulation I without the pseudoceramide 4 was prepared in the form of milk lotion, of which composition is found in Table 5.

TABLE 5

| Ingredients | Amount (wt %) |
| --- | --- |
| Pseudoceramide 4 | — |
| Glycerine | 5.1 |
| Propylene glycol | 4.2 |
| Tocopheryl acetate | 3.0 |
| Liquid paraffin | 4.6 |
| Stearic acid | 1.0 |
| Squalene | 3.1 |
| 1,3-butylene glycol | 2.5 |
| Polysorbate 60 | 1.6 |
| Sepigel 305 | 1.6 |
| Lipoid | 0.6 |
| Waglinol 31918 | 1.5 |
| Perfume | Minute quantity |
| Preservative | Minute quantity |
| Distilled water | To 100 |

Comparative Formulation II

Comparative formulation II without the pseudoceramide 4 was prepared in the form of nutrient cosmetic cream, of which composition is found in Table 6.

TABLE 6

| Ingredients | Amount (wt %) |
| --- | --- |
| Pseudoceramide 4 | — |
| Glycerine | 4.0 |
| Vaseline | 3.5 |
| Triethanol amine | 2.1 |
| Liquid paraffin | 5.3 |
| Squalene | 3.0 |
| Wax | 2.6 |
| Tocophery acetate | 5.4 |
| Polysorbate 60 | 3.2 |
| Carboxyvinyl polymer | 1.0 |
| Sorbitan sesquinoleate | 3.1 |
| Perfume | Minute quantity |
| Preservative | Minute quantity |
| Distilled water | To 100 |

Experimental Example I

Evaluation on Moisturizing Maintenance Effect

Moisturizing maintenance effect of formulations II and III and comparative formulations I and II was tested as follows:

I-1: Examination of Moisture-Retaining Capacity

In a constant temperature and humidity room at a temperature of 22° C. under relative humidity of 45%, each of cosmetic compositions indicated above (0.03 g/16 cm') was topically applied to the inward region of the forearm of 30 persons and then well scrubbed. Water content of the skin treated was measured prior to application and 1 hr and 2 hr after application. The measurement apparatus employed is corneometer CM820 (Conrage+Khazaka), measuring the electric capacity of skin varied depending on water content.

TABLE 7

| Electrical conductivity | Form. II | Form. III | Com. Form. I | Com. Form. II |
|---|---|---|---|---|
| Prior to application | 50 | 50 | 50 | 50 |
| 1 hr after application | 105 | 113 | 76 | 77 |
| 2 hr after application | 86 | 90 | 60 | 63 |

As demonstrated in Table 7, the cosmetic compositions comprising the pseudoceramide of this invention exhibit excellent moisture-retaining capacity as compared to the cosmetic compositions without the pseudoceramide.

I-2: Measurement of Transdermal Water Loss

By means of tape stripping on humeral region of the forearm, the protective barrier of skin was damaged. Thereafter, in a constant temperature and humidity room at a temperature of 22° C. under relative humidity of 45%, each of cosmetic compositions indicated above (0.03 g/16 cm') was topically applied to the inward region of the forearm of 30 persons and then well scrubbed. The amount of transdermal water loss was measured every 8 hours with TEWL meter (Koln-Germany). The respective measurement was performed 5 times at an interval of 5 min and the mean value was calculated.

TABLE 8

| Time after application | Amount of Transdermal Water Loss | | | |
|---|---|---|---|---|
| | Form. II | Form. III | Com. Form. I | Com. Form. II |
| 0 hr | 4.0% | 4.0% | 4.0% | 4.0% |
| 8 hr | −9.3% | −9.9% | −5.7% | −5.2% |
| 16 hr | −7.6% | −8.1% | −0.5% | 0.4% |
| 24 hr | −5.9% | −6.0% | 3.6% | 4.0% |
| 36 hr | −3.1% | −3.9% | 4.0% | 4.0% |

As indicated in Table 8, the cosmetic compositons comprising the pseudoceramide of this invention show significantly lower transdermal water loss as compared to the cosmetic compositions without the pseudoceramide.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A pseudoceramide represented by the following formula (II):

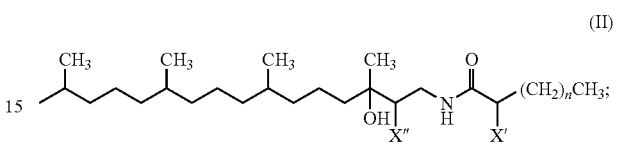

wherein X' represents H or —OH; X" represents —OH,

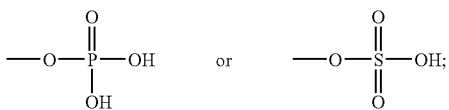

and n is 0 or an integer of from 1 to 47.

2. A cosmetic composition for skin care comprising (a) the pseudoceramide according to claim 1 as active ingredient; and (b) a cosmetically acceptable carrier.

3. The cosmetic composition according to claim 2, wherein the pseudoceramide is present in an amount of 0.0001-10.0 wt % based on the total weight of the composition.

4. The composition according to claim 2, wherein the cosmetic composition is effective in enhancing moisture-retaining property of skin.

5. The composition according to claim 4, wherein the cosmetic composition is in the form of one selected from the group consisting of a solution, a suspension, an emulsion, a paste, an ointment, a gel, a cream, a lotion, a powder, a soap, a surfactant-containing cleanser, an oil, a powder foundation, an emulsion foundation, a wax foundation and a spray.

* * * * *